(12) United States Patent
Gabriel et al.

(10) Patent No.: US 7,264,931 B2
(45) Date of Patent: Sep. 4, 2007

(54) METHOD FOR SEQUENCING NUCLEIC ACID SEQUENCES WITHOUT CHAIN TERMINATION

(75) Inventors: Abram Gabriel, Princeton, NJ (US); Yoshifumi Kobayashi, Highland Park, NJ (US)

(73) Assignee: Rutgers, the State University of New Jersey, New Brunswick, NJ (US)

( * ) Notice: Subject to any disclaimer, the term of this patent is extended or adjusted under 35 U.S.C. 154(b) by 496 days.

(21) Appl. No.: 10/344,891

(22) PCT Filed: Sep. 5, 2001

(86) PCT No.: PCT/US01/27641

§ 371 (c)(1), (2), (4) Date: Jun. 30, 2003

(87) PCT Pub. No.: WO02/20843

PCT Pub. Date: Mar. 14, 2002

(65) Prior Publication Data

US 2004/0014076 A1    Jan. 22, 2004

Related U.S. Application Data

(60) Provisional application No. 60/230,390, filed on Sep. 6, 2000.

(51) Int. Cl.
*C12Q 1/68* (2006.01)
*C12P 19/34* (2006.01)
*C07H 19/00* (2006.01)

(52) U.S. Cl. .................... 435/6; 435/91.2; 536/22.1

(58) Field of Classification Search .............. 435/6, 435/91.2; 536/22.1, 24.33
See application file for complete search history.

(56) References Cited

U.S. PATENT DOCUMENTS

| | | | |
|---|---|---|---|
| 5,756,285 A | 5/1998 | Fuller | 435/6 |
| 5,858,731 A | 1/1999 | Sorge et al. | 435/91.1 |
| 5,994,058 A * | 11/1999 | Senapathy | 435/6 |

OTHER PUBLICATIONS

Kofoid et al. The 17-gene ethanolamine (eut) operon of salmonella typhimurium encodes five homologues of carboxysome shell proteins. J Bacteriol., vol. 181, No. 17, pp. 5317-5329, 1999.*

* cited by examiner

*Primary Examiner*—Suryaprabha Chunduru
(74) *Attorney, Agent, or Firm*—Licata & Tyrrell P.C.

(57) ABSTRACT

A method is provided for determining the sequence of a nucleic acid sequence via incubation of a primer extended product of the nucleic acid sequence in separate pools of semi-random oligonucleotides of 5' $(N)_n A3'$, 5' $(N)_n G3'$, and 5' $(N)_n T3'$, wherein N is A, C, G or T and n is selected so that the oligonucleotides will optimally anneal to all complementary sequences.

4 Claims, No Drawings

US 7,264,931 B2

METHOD FOR SEQUENCING NUCLEIC ACID SEQUENCES WITHOUT CHAIN TERMINATION

This application is a 371 of PCT/US01/27641 filed on Sep. 5, 2001 which claims benefit of 60/230,390 filed on Sep. 6, 2000.

INTRODUCTION

This invention was supported in part by funds from the U.S. government (NIH Grant No. R29AI39201) and the U.S. government may therefore have certain rights in the invention.

FIELD OF THE INVENTION

The present invention provides a new method for sequencing nucleic acid sequences, in particular DNA and RNA, without the need for cloning or PCR or extensive prior knowledge of the region to be sequenced.

BACKGROUND OF THE INVENTION

Various methods for sequencing of nucleic acid sequences have been described. See, e.g. Carothers et al. Biotechniques 1989 7:494-499; Donis-Keller et al. Nucleic Acids Res. 1977 4:2527-2538; Maxam, A. M. and Gilbert, W. Proc. Natl Acad. Sci. USA 1977 74:560-564; Sanger et al. Proc. Natl Acad. Sci. USA 1977 74:5463-5467; and Wong et al. Nature 1987 330:384-386. These methods typically require cloning or otherwise purifying the sequence of interest, performance of polymerase chain reaction, or extensive knowledge of the region of the nucleic acid sequence to be determined. Further, fairly large amounts of the nucleic acid to be sequenced are generally required.

SUMMARY OF THE INVENTION

An object of the present invention is to provide a method for determining the sequence of nucleic acids which comprises linearly amplifying a nucleic acid sequence using a DNA polymerase and a unique first primer which is complementary to a known portion of the nucleic acid sequence to produce a first primer extended product that serves as a template for the next step; incubating the first primer extended product with dNTPs and DNA polymerase and with separate pools of semi-random oligonucleotide primers comprising 5' $(N)_nA3'$, 5' $(N)_nC3'$, 5' $(N)_nG3'$, and 5' $(N)_nT3'$, wherein N=A, C, G or T and n is selected so that the oligonucleotides will optimally anneal to all complementary sequences and be extended, to produce a pool of second primer-extended products; incubating each pool of products with dNTPs and DNA polymerase and with a unique second detectably labeled primer which is complementary to a known portion of the nucleic acid sequence of interest to produce detectably labeled extension products via linear amplification; separating the detectably labeled extension products from each pool via gel electrophoresis; and reading the sequence of the detectably labeled extension products via autoradiography, a fluorescence detector or other sequence detection systems.

DETAILED DESCRIPTION OF THE INVENTION

The present invention relates to a new method for sequencing nucleic acid sequences including, but not limited to genomic DNA, oligonucleotide primers, PCR products, viral DNA and plasmid DNA, as well as cDNA derived from reverse transcribed RNA. Using the method of the present invention, the sequence of genomic DNA can be determined without requiring cloning, PCR amplification or extensive prior knowledge. Further, sequencing does not require primer extension with dideoxynucleotides for chain termination, thereby minimizing the inherent background associated with direct genomic sequencing by standard methods. The method of the present invention can also be used to determine RNA sequences such as mRNA based only upon knowing approximately 20 to 30 bases of the unique 3' sequence, using a cDNA generated from the RNA by reverse transcriptase. Knowledge of the sequence of these bases, used to design primers, can be derived from various sources and/or techniques, including but not limited to, prior expressed sequence tags, cDNA cloning or RACE methods, or from previously sequenced genomic DNA with which to design primers. In addition, this method can be used to determine the sequence of DNA and RNA obtained from organisms which cannot be cultured and which are available only in limiting amounts.

The method of the present invention comprises four steps, with the second step distinguishing the method of the present invention from prior art sequencing methods.

In the first step, the nucleic acid sequence, e.g. the genomic DNA, to be sequenced is linearly amplified using a first primer which is complementary to a known portion of the nucleic acid sequence. In a preferred embodiment, the first primer is modified by biotinylating the 5' most base to facilitate purification of the extended product. Other means for modification to facilitate purification including, but not limited to, labeling with digoxygenin at the 5' most base which will bind to a digoxygenin specific antibody or inclusion of a specific 5' sequence tag that can hybridize to a bound complementary sequence, can also be used. Extension of the first primer is accomplished using a heat stable polymerase. Multiple extensions of at least 10 and possibly hundreds depending upon the rarity of the template are performed to produce a first primer extension product. The first primer extension product is then purified, preferably via an affinity separation technique such as gel filtration or separation via magnetic beads coated with streptavidin. However, linear amplification as performed in this first step is performed routinely by those of skill in the art. Thus, modifications to this first step can be made.

In contrast to other sequencing methods which use chain termination with dideoxynucleoside triphosphates or chemical cleavage, in the second step of the method of the present invention, the first primer extension product is incubated with four separate pools of semi-random oligonucleotides. Each pool of semi-random oligonucleotides comprises either 5' $(N)_nA3'$, 5' $(N)_nC3'$, 5' $(N)_nG3'$, or 5' $(N)_nT3'$, wherein N is A, C, G, or T and n is selected so that the oligonucleotides will optimally anneal to all complementary sequences and be extended. Preferably n ranges from 3 to 10 depending upon the specific application. However, as will be understood by those of skill in the art upon reading this disclosure, the n may be varied for other applications. Each pool also comprises dNTPs, a DNA polymerase and its appropriate buffer. After annealing, the polymerase extends the semi-random oligonucleotides which serve as primers using the first primer extension product as a template.

In step 3, the products of each of the four reactions are separately incubated with a second primer. The second primer can be identical to the first primer. Alternatively, the second primer can be complementary to a known portion of the sequence downstream of the first primer. For each reaction, linear amplification is carried out using a heat stable polymerase and a variable number of amplification cycles. Examples of heat stable polymerases include, but are not limited to, TAQ polymerase, VENT polymerase, PFU polymerase and TTH polymerase. In a preferred embodiment, the second primer is detectably labeled at the 5' end to allow for easy detection of extension products. Examples of detectable labels include, but are not limited, to radiolabels such as $^{32}P$, and $^{33}P$, as well as fluorescent dyes such as fluorescein, rhodamine, Texas red, and Oregon green.

$(N)_5G3'$, and 5' $(N)_5T3'$ were combined separately with 0.5 units of polymerase in 10 μl of Klenow buffer containing 0.2 M HEPES, pH 6.8, 2.5 mM MgCl and 0.01 pmoles of the template, and 300 μM each dNTPs and incubated under conditions which foster polymerization of the semi-random oligonucleotide primers.

The extended products of these pools were then incubated with a second primer, a 19 base 5' $^{32}P$ end-labeled oligonucleotide corresponding to the 5' end of the 75 mer oligonucleotide and Taq polymerase. The sequence of this primer was 5' CCC CTC GAG GTA AAC GGC G3' (SEQ ID NO:2) and was 5' end labeled with $^{32}p$ using T4 polynucleotide kinase and γ $^{32}P$ ATP.

The resulting products of the pools were separated via polyacrylamide gel electrophoresis, autoradiographed and 43 bases of the downstream sequence were accurately sequenced.

SEQUENCE LISTING

<160> NUMBER OF SEQ ID NOS: 2

<210> SEQ ID NO 1
<211> LENGTH: 75
<212> TYPE: DNA
<213> ORGANISM: Artificial Sequence
<220> FEATURE:
<223> OTHER INFORMATION: Description of Artificial Sequence: Synthetic

<400> SEQUENCE: 1
cccctcgagg taaacggcgg gagtaactat gactctctta aggtagccaa atgcctcgtc      60
atctaactcg agccc                                                      75

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic

<400> SEQUENCE: 2
cccctcgagg taaacggcg                                                  19

In the fourth step, reaction products are purified, preferably via size exclusion chromatography, and loaded onto a denaturing polyacrylamide gel to separate the reaction products according to size. Other purification methods useful in the present invention include, but are not limited to, ethanol precipitation and membrane filtration. The products are then detected, preferably via the detectable label of the second primer using either autoradiography or a fluorescence absorbance detector as used in conventional automated sequencing machine.

The following nonlimiting example is provided to further illustrate the present invention.

EXAMPLE

A 75 mer oligonucleotide, 5' CCC CTC GAG GTA AAC GGC GGG AGT AAC TAT GAC TCT CTT AAG GTA GCC AAA TGC CTC GTC ATC TAA CTC GAG CCC 3' (SEQ ID NO:1) was used directly as a template for step 2 of the method of the present invention. Four pools of semi-random oligonucleotides of the form 5' $(N)_5A3'$, 5' $(N)_5C$ 3', 5'

What is claimed is:

1. A method for sequencing a nucleic acid sequence comprising:
  (a) linearly amplifying the nucleic acid sequence using a first primer which is complementary to a known portion of the nucleic acid sequence to produce a first primer extended product;
  (b) incubating the first primer extended product with dNTPs, a DNA polymerase, and separate pools of semi-random oligonucleotide primers consisting of 5' $(N)_nA3'$, 5' $(N)_nC3'$, 5' $(N)_nG3'$, and 5' $(N)_nT3'$, wherein N is A, C, G or T and n is selected so that the oligonucleotides will optimally anneal to all complementary sequences, thereby generating four pools of primer extended products;
  (c) incubating each of the four pools of primer extended products with a second detectably labeled primer which is complementary to a known portion of the nucleic acid sequence to produce detectably labeled extension products via linear amplification; and (d) separating the detectably labeled extension products by size; and (e) reading the sequence of the detectably labeled extension products via an automated sequencing machine.

2. The method of claim 1 wherein the nucleic acid sequence is genomic DNA.

3. The method of claim 1 wherein the nucleic acid is a DNA selected from the group consisting of oligonucleotide primers, PCR products, viral DNA and plasmid DNA.

4. The method of claim 1 wherein the nucleic acid sequence is cDNA derived from RNA by reverse transcriptase.

* * * * *